United States Patent [19]

Kaufman et al.

[11] Patent Number: 5,259,384
[45] Date of Patent: Nov. 9, 1993

[54] ULTRASONIC BONE-ASSESSMENT APPARATUS AND METHOD

[76] Inventors: Jonathan J. Kaufman, 112 Willow St.-#1-A, Brooklyn, N.Y. 11201; Alessandro E. Chiabrera, Viale Cambiaso 1/15, 16145 Genoa, Italy

[21] Appl. No.: 922,136
[22] Filed: Jul. 30, 1992
[51] Int. Cl.$^5$ ............................................. A61B 8/00
[52] U.S. Cl. ......................... 128/660.01; 128/660.02; 128/660.06; 128/661.03
[58] Field of Search ...................... 128/660.01, 660.02, 128/660.06, 660.07, 661.04; 364/413.25

[56] References Cited

U.S. PATENT DOCUMENTS

4,913,157 4/1990 Pratt, Jr. et al. ............... 128/661.03
4,976,267 12/1990 Jeffcott et al. ............... 128/660.02 X
5,119,820 6/1992 Rossman et al. ............ 128/660.01 X

*Primary Examiner*—Francis Jaworski
*Attorney, Agent, or Firm*—Hopgood, Calimafde, Kalil, Blaustein & Judlowe

[57] ABSTRACT

Non-invasive, quantitative in-vivo ultrasonic evaluation of bone is performed by subjecting bone to an acoustic excitation pulse supplied to one of two transducers on opposite sides of the bone, and involving a composite sine-wave signal consisting of repetitions of plural discrete ultrasonic frequencies that are spaced at approximately 2 MHz. Signal-processing of received signal output of the other transducer is operative to sequentially average the most recently received given number of successive signals to obtain an averaged per-pulse signal and to produce a Fourier transform of this signal. In a separate operation, the same transducer responds to the transmission and reception of the same excitation signal via a medium of known acoustic properties and path length to establish a reference signal, which is processed to produce its Fourier transform. The two Fourier transforms are comparatively evaluated to produce a bone-transfer function, which is then processed to derive the frequency-dependent specific-attenuation and group-velocity functions $\mu(f)$ and $Vg(f)$ associated with the bone-transfer function. The function $Vg(f)$ is related to the derivative of the phase of the bone-transfer function, as a function of frequency. A neural network, configured to generate an estimate of one or more of the desired bone-related quantities, is connected for response to the functions $\mu(f)$ and $Vg(f)$, whereby to generate the indicated estimates of bone status, namely, bone-density, bone-strength and fracture risk.

32 Claims, 3 Drawing Sheets

ULTRASONIC BONE-ASSESSMENT APPARATUS AND METHOD

BACKGROUND OF THE INVENTION

The invention pertains to apparatus and methods for non-invasively and quantitatively evaluating the status of bone tissue in vivo, as manifested, at a given time, through one or more of the quantities: bone-mineral density, strength, and fracture risk.

In recent years, various attempts have been made to use ultrasonic energy to assess the condition of bone tissue, in vivo, but these attempts have been essentially ad hoc, with no consistent framework within which to analyze data. A great deal of information is obtainable from ultrasonic experiments, but much of the information has not been used. The signal-processing techniques that have been used have been so simple as to ignore available and useful aspects of the data, and the signal-to-noise ratio of experimental data has been relatively poor.

U.S. Pat. No. 3,847,141 to Hoop discloses a device to measure bone density as a means of monitoring calcium content of the involved bone. A pair of opposed ultrasonic transducers is applied to opposite sides of a patient's finger, such that recurrent pulses transmitted via one transuducer are "focused" on the bone, while the receiving response of the other transducer is similarly "focused" to receive pulses that have been transmitted through the bone. The circuitry is arranged such that filtered reception of one pulse triggers the next pulse transmission; the filtering is by way of a bandpass filter, passing components of received signals, only in the 25 to 125 kHz range; and the observed frequency of retriggering is said to be proportional to the calcium content of the bone. Thus, Hoop is not concerned with anything more than what he perceives to be transit time for pulses in the indicated band.

Pratt, Jr. is identified with a number of U.S. patents, including Nos. 4,361,154, 4,421,119 (divisionally related to the '154 patent, and subsequently reissued, as Re. No. 32,782), 4,913,157, and 4,941,474, all dealing with establishing, in vivo, the strength of bone in a live being such as a horse. In the first three of his patents, the inventor bases his disclosures on the measurement of transit time from "launch" to "reception" of pulses of 0.5 MHz and 1.0 MHz through the bone and soft tissue, and from measurement of pulse-echo time, to thereby derive a measurement of transit time through bone alone. A data bank enables his evaluation of the meaning of variations in measurements of transit time, which the inventor deduces to be propagation velocity through each measured bone. The inventor's U.S. Pat. No. 4,913,157 operates on the same general principle of transit-time/velocity deduction, using the later preferred frequency of 2.25 MHz as the base frequency of pulsed "launchings", and he purports to derive the bone-transfer function from analysis of an average of received pulses. In his U.S. Pat. No. 4,941,474, the inventor further refines his technique of transit-time/velocity deduction, inter alia, by separately determining the ratio of the velocity of his observed "bone signal" to the velocity of his observed "soft-tissue signal", using the technique of matched filtering/Fourier transform filtering set forth in his U.S. Pat. No. 4,913,157.

Palmer et al. U.S. Pat. No. 4,774,959 discloses apparatus for deriving the slope of the relation between ultrasonic frequency and attenuation, for the case of a sequence of tone signals, in the range 200 to 600 kHz, applied to one transducer and received by another transducer, (a) after passage through a heel bone, in comparison with (b) passage between the same two transducers without the intervening presence of the heel. The assumption necessarily is that the frequency/attenuation relation is a straight line, i.e. of constant slope.

Brandenburger U.S. Pat. No. 4,926,870 discloses another in vivo bone-analysis system which depends upon measuring transit time for an ultrasonic signal along a desired path through a bone. A "Canonical" wave form, determined by previous experience to be on the correct path, is used for comparison against received signals for transmission through the patient's bone, while the patient's bone is reoriented until the received signal indicates that the patient's bone is aligned with the desired path. Again, ultrasonic velocity through the patient's bone is assumed to have been determined from measured transit time.

Rossman et al. U.S. Pat. No, 5,054,490 discloses an ultrasound densitometer for measuring physical properties and integrity of a bone, upon determination of transit time, in vivo, through a given bone, in comparison with transit time through a medium of known acoustic properties; alternatively, the Rossman et al. device compares absolute attenuation of specific frequency components of ultrasound acoustic signals through the bone with the absolute attenuation of the same frequency components through a medium of known acoustic properties. For attenuation measurements, a "broad-band ultrasonic pulse" is recommended and is illustrated as a single spike "which resonates with a broadband ultrasonic emission". The necessary comparisons are performed by a microprocessor, resulting in a slope of attenuation versus frequency in the broadband of interest. The frequencies or frequency ranges are not disclosed.

The prior art, exemplified by the references that have been briefly discussed, proceed on the assumptions either that transit time is all-important in assessing acoustic velocity or that only one or a few specific ultrasonic frequencies are significant in the determination of the attenuation versus frequency "slope" of a presumably linear relationship. However, the present inventors have found that the attenuation versus frequency relation for bone is non-linear, over the range of ultrasonic frequencies of likely interest, namely, up to approximately 2 MHz, and that potentially significant data exist and have been discarded or overlooked in the prior art through a preoccupation with measuring transit time and/or the velocity of ultrasonic acoustic propagation through bone and soft tissue. Moreover, prior efforts to achieve a broadband analysis have overlooked a need to assure adequate signal above noise throughout a relevant broadband of ultrasonic frequencies.

BRIEF STATEMENT OF THE INVENTION

It is accordingly an object of the invention to provide an improved method and apparatus for non-invasive and quantitative evaluation of bone tissue in vivo.

Another object is to meet the above object, such that bone-mineral density, strength, and fracture risk may be readily and more reliably evaluated than heretofore.

A specific object is to achieve the above objects with a broadband approach wherein ultrasonic signal sufficiently exceeds noise throughout the broadband, to enable evaluation of received signal above noise, throughout the broadband ultrasonic region to about 2 MHz.

It is a general object to achieve the foregoing objects with apparatus components that are commercially available.

Briefly stated, the invention in its presently preferred form achieves the foregoing objects by iteratively subjecting bone to an ultrasonic acoustic excitation signal pulse of finite duration, supplied to one of two transducers on opposite sides of the bone, and involving a composite sine-wave signal consisting of plural discrete frequencies that are spaced in the ultrasonic region to approximately 2 MHz; the excitation signal is repeated substantially in the range 1 to 1000 Hz. Signal-processing of received signal output of the other transducer is operative (a) to sequentially average the most recently received given number of successive signals to obtain an averaged per-pulse signal and (b) to produce a Fourier transform of the averaged per-pulse signal. In a separate operation not involving the bone, the same transducers respond to the transmission and reception of the same excitation signal via a medium of known acoustic properties and path length to establish a reference signal, and this reference signal is processed to produce the Fourier transform of the reference signal. The two Fourier transforms are comparatively evaluated to produce a bone-transfer function, and the bone-transfer function is processed to derive the frequency-dependent specific-attenuation function $\mu(f)$ and the frequency-dependent group-velocity function $v_g(f)$ associated with the bone-transfer function; specifically, the frequency-dependent group velocity function $v_g(f)$ is related to the derivative of the phase of the bone-transfer function, as a function of frequency. Finally, a neural network, configured to generate an estimate of one or more of the desired bone-related quantities, is connected for response to the specific-attenuation function $\mu(f)$ and to the group-velocity function $v_g(f)$, whereby to generate the indicated estimates of the status of bone that is being analyzed.

DETAILED DESCRIPTION OF THE INVENTION

The invention will be described in detail for a presently preferred embodiment, in conjunction with the accompanying drawings, in which.

Figure 1:
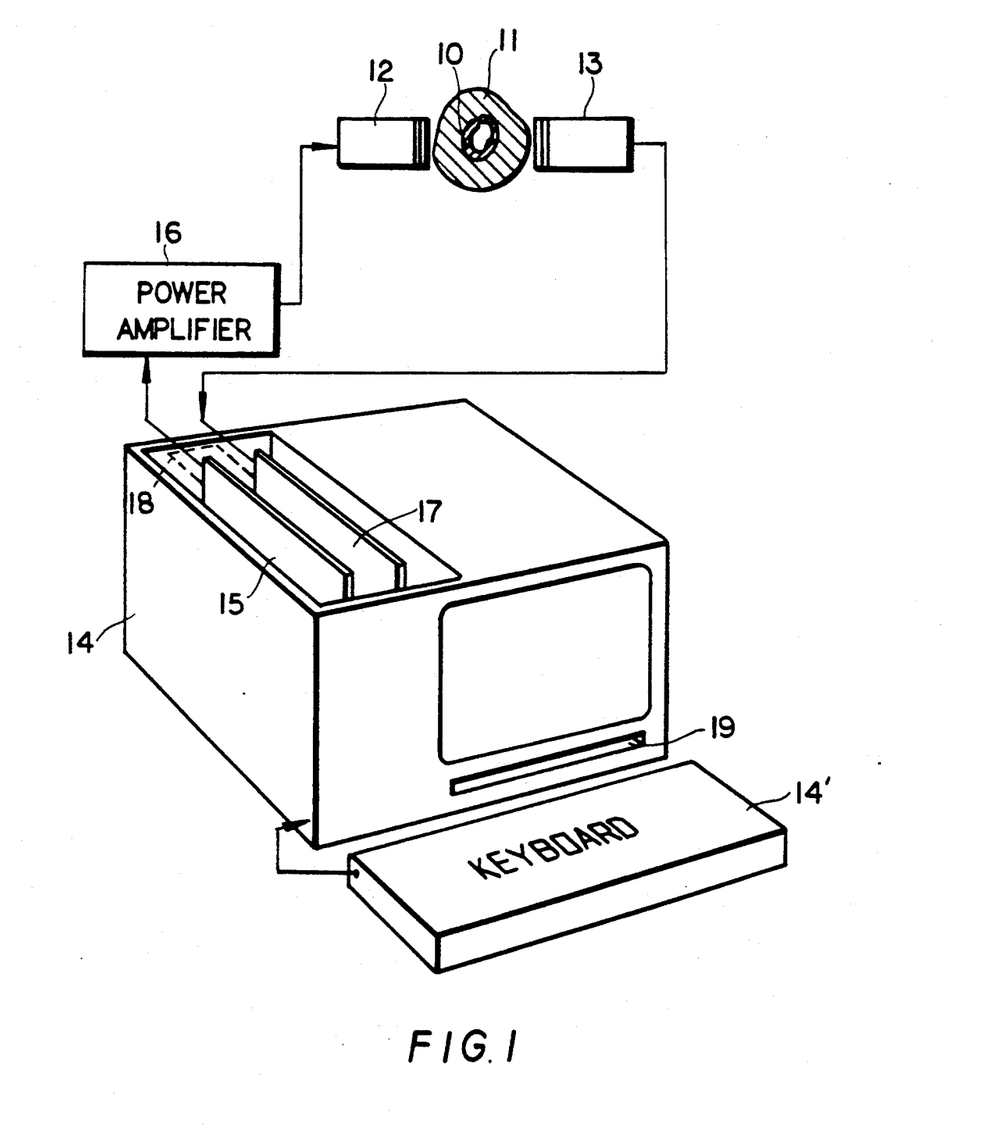
FIG. 1 is an electrical-circuit diagram schematically showing the interconnected relation of components of apparatus of the invention.

The invention is shown in FIG. 1 in application to interconnected components for constructing apparatus for performing methods of the invention, namely, for non-invasively and quantitatively evaluating the status of bone tissue in vivo, as manifested through one or more of the quantities: bone-mineral density, strength, and fracture risk at a given time. These components are, in general, commercially available from different sources and will be identified before providing detailed description of their total operation.

In FIG. 1, the bone locale 10 to be analyzed in vivo is shown surrounded by soft tissue 11 and to be interposed between two aligned and opposed ultrasonic transducers 12, 13, which may be identically the same, and obtainable from Panametrics, Inc., Waltham, Mass.; suitably, each of transducers 12, 13 may be Panametrics "VIDEOSCAN" part number V318-SU, having a nominal element size of ¾-inch diameter, and rated for 500 kHz. As shown, transducer 12 is used for signal launching and transducer 13 is the receiver of the launched signals after passage through bone 10, through its surrounding soft tissue 11, and through a coupling medium such as a gel between each transducer face and outer skin of the soft tissue 11.

Basic operation is governed by computer means 14, which may be a PC computer, such as the "25 MHz 386" available from Gateway 2000, Inc., North Sioux City, S.D.; as its designation suggests, this computer contains a 25 MHz clock-pulse generator, and an Intel 80386 processor, with provision for keyboard instruction at 14'.

An arbitrary function-generator card 15 is shown installed in the computer. This card is relied upon to generate an excitation signal which is periodically supplied to the launch transducer 12, via power amplifier means 16. The power amplifier is suitably Model No. 240L, an RF power-amplifier product of EIN, Inc., Rochester, N.Y. This product provides a 50 dB gain, over the range 20 kHz to 10 MHz.

The excitation signal generated by card 15 is a finite-duration composite sine-wave signal, consisting of plural discrete frequencies that are spaced in the ultrasonic spectral region to approximately 2 MHz, and this excitation signal is repeated substantially in the range 1 to 1000 Hz. Card 15 may suitably be a waveform synthesizer product of Quatech, Inc., Akron, Ohio, identified by Quatech part No. WSB-100. This waveform synthesizer provides generation of analog signals independent of the host computer 14, allowing full processor power to be used for other tasks, including calculation of waveform data; it has the capacity to generate an output signal comprising literally thousands of points in the indicated ultrasonic frequency region.

Another card 17 is also shown installed in the computer for converting signals received at 13 in digital format for further processing in computer 14. Card 17 may suitably be a 100 MHz waveform digitizer, part number "STR*8100", a product available from SONIX, of Springfield, Va. A connection 18 is shown by dashed lines, connecting the signal-generator card 15 to the A/D card 17, for synchronizing purposes and for the purposes of digitizing the excitation signals, to enable computer 14 to perform a suitably compensated, continuously operative updating average of the signals received at 13.

Finally, general signal-processing/display/storage software, for the signal-processing control and operation of the computer is not shown but will be understood to be a floppy disk loaded at 19 into the computer; this software is suitably the MATLAB-386, available from The Math Works, Inc., Natick, Mass. Further software, also not shown but loaded into the computer, is neural-network software, identified as EXPLORENET 3000, a product of HNC, Inc., San Diego, Calif.

In the presently preferred embodiment, involving the described components of FIG. 1, the same components are utilized not only for performing the continuously updated averaging of the latest succession of signals received at 13, but also for establishing and entering into computer storage the Fourier transform of a reference signal that is obtained by removing the body part 10, 11 from the space between transducers 12, 13.

Computer operation on the updated average of the received signals will be referred to as the averaged per-pulse signal, and this averaged per-pulse signal is also signal-processed in the computer into the Fourier transform of the averaged per-pulse signal.

The computer will be understood to be further programmed to comparatively and continuously evaluate the Fourier transform of the currently averaged per-pulse signal, against the Fourier transform of the reference signal, thereby producing a bone-transfer function. Still further, the computer will be understood to be programmed to process the bone-transfer function to derive the frequency-dependent specific-attenuation function $\mu(f)$ and the frequency-dependent group-velocity function $v_g(f)$ associated with the bone-transfer function. Finally, these two functions, for each of the large plurality of involved frequencies in the composite sine-wave signal are supplied within the computer to the neural network, it being understood that the neural network will first have been trained and configured to generate an estimate of one or more of the above-indicated and currently analyzed bone properties, namely, bone-mineral density, strength, and fracture risk.

In the presently preferred embodiment of the invention and with additional reference to the flow diagram of FIG. 2, data is collected and processed as follows. A bony member (10, 11) is placed between two ultrasound transducers (12, 13). An ultrasound signal is transmitted from transducer (12), passes through the bony member, and is received by the other transducer (13). The transmitted ultrasound signal is generated using a finite-duration composite sine-wave signal. A single repetition of this waveform is described by $$v(t) = \sum_{i=0}^{N} a_i \sin(2\pi f_i t + \phi_i), \quad 0 \leq t \leq T \tag{1}$$

where $a_i$ and $\phi_i$ are the amplitude and phase, respectively, associated with frequency $f_i, i=1, \ldots, N$, and T is chosen to be at least two times longer than the period of the lowest frequency $f_1$. The frequencies $f_i$ are selected from within the range 25 kHz–2 MHz. In this preferred embodiment, the lowest frequency $f_1 = 100$ kHz, T = 20 microseconds, and the frequency range is 100 kHz–800 kHz, with 50 kHz intervals, for a total of N = 15 frequencies. The phases $\phi_i$ are pseudo-random numbers distributed uniformly between 0 and $2\pi$. This ensures that peak amplitudes are minimized for fixed signal power. The amplitudes, $a_i$, are chosen according to the relationship $$a_i \propto \frac{\exp(Bf_i)}{|H_r(f_i)|} \tag{2}$$

In this expression, B is the attenuation of an average bony member and $|H_r(f_i)|$ is the magnitude transfer function of the overall ultrasound measurement system when a medium of negligible attenuation is placed between the two transducers. In this preferred embodiment of the invention, B=10 nepers MHz$^{-1}$, and $|H_r(f_i)|$ is the magnitude Fourier transform of the received waveform after it has propagated through water using an impulsive-type input signal. This choice for the amplitudes of the composite sine-wave signal ensures that the received signal has approximately constant signal-to-noise ratio throughout the frequency range.

The above waveform is transmitted periodically at a repetition rate of 500 Hz. In the presently preferred embodiment, each received waveform, $s_i(t)$, is averaged a total of 100 times to obtain the averaged per-pulse signal, s(t). Subsequently, the Discrete Fourier Transform (DFT), S(f), of s(t) is obtained using the Fast Fourier Transform (FFT) algorithm.

A reference signal, r(t) is also obtained by averaging 100 ultrasound signals transmitted through water only, i.e., by removing the bony member and replacing it with water. The same composite sine wave input signal is used for generation of the reference signal, in order that the bone-transfer function be obtained as shown below. The DFT, R(f), of the reference signal is then obtained using the FFT.

The data is further processed to obtain the bone transfer function, H(f), where $$H(f) \triangleq \frac{S(f)}{R(f)} \tag{3}$$

H(f) is processed further to obtain the frequency-dependent specific-attenuation function, $\mu(f)$, and frequency-dependent group-velocity function, $v_g(f)$:

$$\mu(f) = -\log(|H(f)|^{1/L}) \tag{4}$$

and $$v_g(f) = \frac{1}{\frac{1}{2\pi} \frac{d\beta}{df} + \frac{1}{v_w}} \tag{5}$$

where $$\beta(f) = -\frac{\arg[H(f)]}{L} \tag{6}$$

Here, $v_w$ is the velocity of ultrasound in water, L is the thickness of the bony member, and arg[H(f)] evaluates the phase of the complex bone transfer function, H(f).

The frequency-dependent specific-attenuation, $\mu(f_i)$, and frequency-dependent group-velocity, $v_g(f_i), i=1, \ldots, N$, serve as inputs into an appropriately configured neural network to generate an estimate of one or more of the above-indicated and currently analyzed bone properties, namely, bone-mineral density, strength, and fracture risk. In the presently preferred embodiment, the neural network is a feedforward network with 30 inputs, 1 output, and one hidden layer which consists of 300 processing elements. The network is trained with the backpropagation algorithm to estimate bone mineral density.

The above set of inputs was used to evaluate the ability of the neural network to predict bone mineral density. In this connection, a training set of data was established from 27 bovine trabecular bone cubes for which the ultrasound specific-attenuation, ultrasound group-velocity, and bone mineral density had been measured. Using simple linear regression, the average percent errors for predicting density were 25 and 23 percent for specific-attenuation and group-velocity, respectively. In contrast, the neural network provided a 15 percent error in predicting density, representing about a 40 percent improvement in prediction accuracy. The neural network was able to nonlinearly combine additional information from the specific-attenuation and group-velocity functions compared with the univariate regressions. Moreover, this neural network based approach does not require any a priori information on the functional form relating specific-attenuation and group-velocity to density (or strength or fracture-risk). It extracts this information from the data itself.

In a variation of the described procedure, both the frequency-dependent specific-attenuation $\mu(f_i)$ and frequency-dependent group-velocity $v_g(f_i), i=1, \ldots, N$, are modelled with polynomials whose coefficients are obtained using linear-least-squares analysis. These coefficients, i.e., $\mu_0, \mu_1, \ldots, \mu_M$ and $v_{g0}, v_{g1}, \ldots, v_{gK}$ serve as inputs to another appropriately configured neural network. In this preferred embodiment, $M=2$ and $K=1$, and the neural network is a feedforward network with 5 inputs, 1 output, and one hidden layer consisting of 50 processing elements. The neural network can also be configured to estimate bone strength and/or fracture risk, in addition to bone density. In these cases, different sets of training data are required to specify the neural network.

In another variation of the described procedure, the transmitting transducer is adapted for measuring the reflected ultrasound waveform in order to obtain an estimate of the traversed soft-tissue thickness. Reflection measurements are made with a Panametrics (Waltham, Mass.) Pulser/Receiver Model #500 PR which excites the transmitting transducer with a narrow pulse and subsequently measures the reflected waveform. The arrival time of the reflected signal provides a measure of the round-trip transit time, $\tau$, for the acoustic pulse to travel from the transducer through the soft-tissue, to the bone surface (where it is partially reflected), and back through the soft tissue. The soft-tissue thickness $d_s$ can then be calculated as $$d_s = v_s \tau \tag{7}$$

where $v_s$ is the velocity of ultrasound in soft tissue and is given by $v_s = 1540$ ms$^{-1}$. Equation (7) includes a factor of two for estimating the soft-tissue thickness on both sides of the bone.

The soft-tissue thickness, $d_s$, may then be used to correct the specific-attenuation, $\mu(f)$, and group-velocity, $v_g(f)$. These corrections are given by $$\mu_{corr}(f) = (\mu(f) - \mu_s(f))\frac{L}{L-d_s} + \mu_s(f) \tag{8}$$

$$v_{g,corr}(f) = \frac{v_g(f)}{\frac{L}{L-d_s} - \frac{d_s}{L-d_s}\frac{v_g(f)}{v_s}} \tag{9}$$

where $\mu_s(f)$ is the specific-attenuation of soft-tissue, and $\mu_{corr}(f)$ and $v_{g,corr}(f)$ are the soft-tissue corrected frequency-dependent specific-attenuation and soft-tissue corrected frequency-dependent group-velocity, respectively. The soft-tissue specific-attenuation is modelled as a linear function of frequency, namely, $\mu_s(f) = 2 \times 10^{-4} f$, where f is the frequency in Hz. Application of the above correction equations (8-9) has a relatively small effect on specific-attenuation (about 0.5%-2%) and a larger effect on group-velocity (4%-10%), depending on the relative amount of soft tissue and acoustic properties of the bony member.

Figure 2:
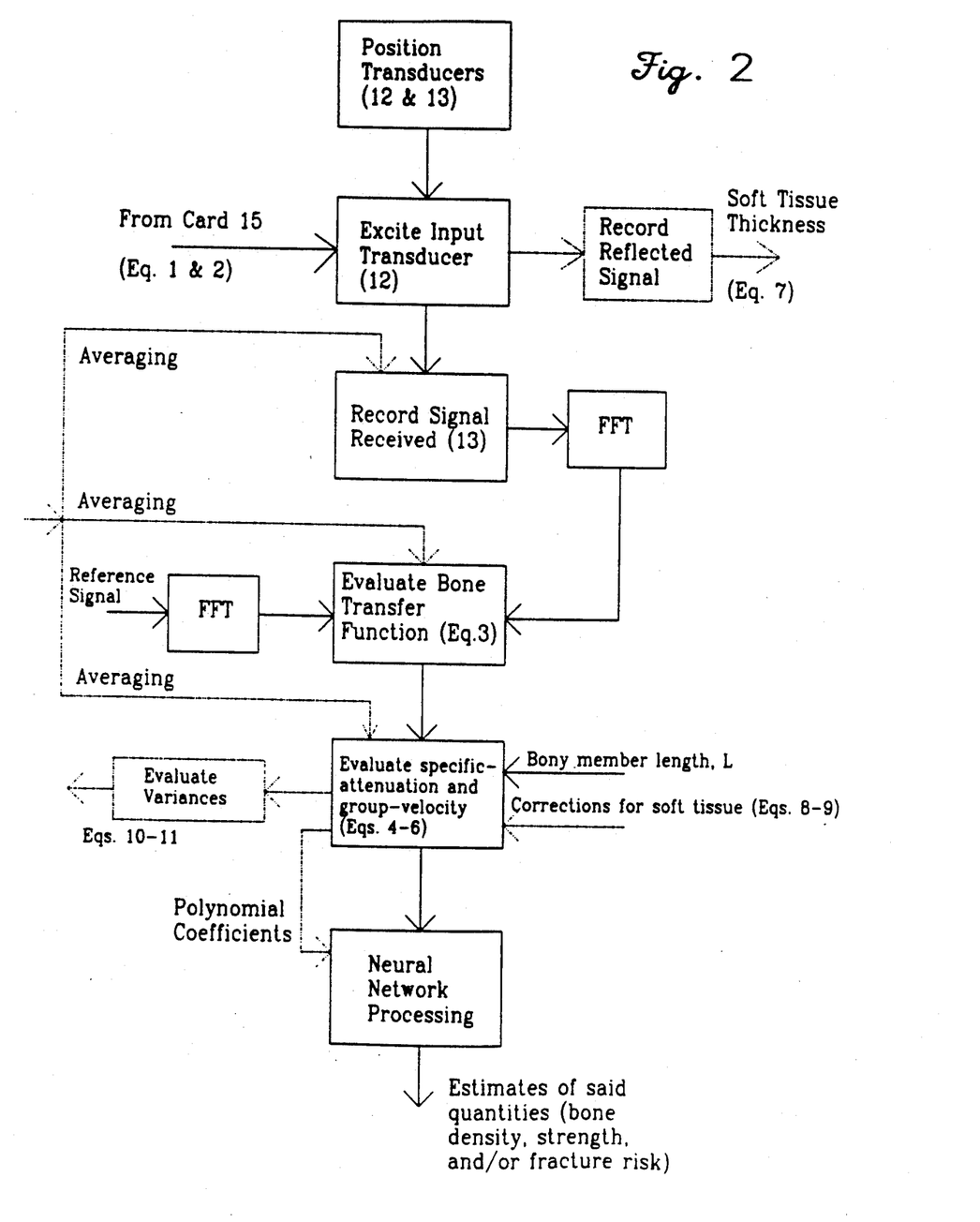
FIG. 2 is, for a first embodiment, a flow chart of computer-controlled operations in automatically analyzing and quantitatively reporting estimates of relevant bone-related factors.

In another variation of the process of FIG. 2, the transmitting and receiving transducers can both be adapted for pulse-echo mode, in order to obtain a more accurate estimate of total traversed soft-tissue thickness, $d_s$. In this embodiment, individual estimates of the soft-tissue thickness on each side of the bone are made in an identical fashion to that described in the above paragraph, and added together to obtain the final estimate. The corrected specific-attenuation and corrected group-velocity are obtained in an identical fashion as in equations (8-9).

In still another variation of the invention, the variance, $\sigma_\mu^2$, of the frequency-dependent specific-attenuation, $\mu(f)$, and the variance, $\sigma_v^2$, of the frequency-dependent group-velocity, $v_g(f)$, are evaluated on-line. The value of the variance, relative to the mean, can be used to determine the time at which sufficient signal averaging has been achieved. Monitoring of the variance can also be used to indicate lack of precision in the data, and that the experimental conditions must be modified. The expressions for recursively calculating the variances are $$\sigma_\mu^2(i) = \frac{1}{i}[\mu_i - \bar{\mu}_i]^2 + \frac{i-1}{i}\sigma_\mu^2(i-1), i = 1, \ldots, \mu_{avg} \tag{10}$$

$$\sigma_v^2(i) = \frac{1}{i}[v_{gi} - \bar{v}_{gi}]^2 + \frac{i-1}{i}\sigma_v^2(i-1), i = 1, \ldots, v_{avg} \tag{11}$$

In these expressions, $\mu_i$ and $v_{gi}$ are the specific-attenuation and group-velocity associated with data-acquisition i, respectively, while the overbar on each represents the current mean value. By comparing the respective variances with the respective mean values (squared), the number of acquisitions ($\mu_{avg}$ and $v_{avg}$) needed to achieve estimates of specific precision can be assessed. For example, in some instances, 1000 acquisitions were required to achieve a relative precision of 0.01 (the ratio of the square root of the variance to mean) in both the specific-attenuation and group-velocity, while in other cases 100 acquisitions were sufficient to attain the same precision.

Figure 3:
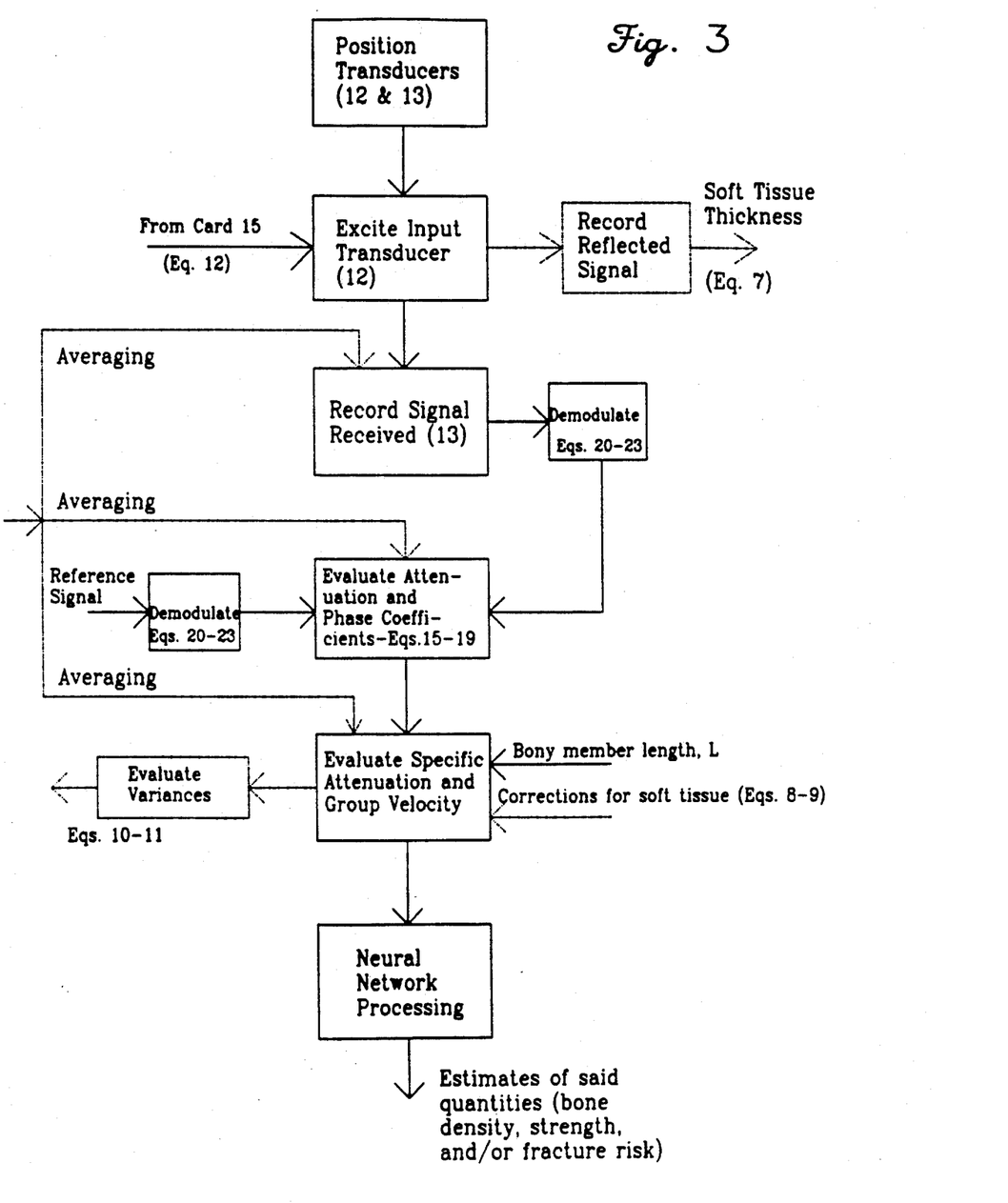
FIG. 3 is a flow chart similar to that of FIG. 2, but for another embodiment.

In the second embodiment of the invention, namely, as indicated in the flow diagram of FIG. 3, direct estimation of the frequency-dependent specific-attenuation and frequency-dependent group-velocity is performed. In this embodiment, an input signal which produces an acoustic pulse with a Gaussian envelope is used. The signal which propagates through the reference medium, r(t), is given by $$r(t) = e^{-\sigma^2 t^2} \cos(\Omega_c^2 t^2 + \omega_c t + \phi_c) \tag{12}$$

The bone-transfer function is assumed to be reasonably well-modelled by the following second-order polynomial expansion of the phase, $\Phi(f)$, and attenuation, $A(f)$*:

$$H(f) \approx e^{-[A0 + A1 2\pi f + A2(2\pi f)^2]} e^{-j[\Phi 0 + \Phi 1 2\pi f + \Phi 2(2\pi f)^2]} \tag{13}$$

*In the variations and embodiments thus far discussed, $\mu(f) = A(f)/L$ and $\beta(f) = \Phi(f)/L$. Thus, knowledge of $A(f)$ and bony member length L give directly the specific-attenuation function, $\mu(f)$. Similarly, $\beta(f)$ may also be used in equation (5) to calculate the group-velocity function, $v_g(f)$.

With the above Gaussian input signal and bone-transfer function approximation, the signal measured at the receiver is $$s(t) = e^{-a_0} e^{-A_{02}(t-\tau_0)^2} \cos[\Omega_0^2(t-\tau_0)^2 + \omega_0 t + \phi_0] \tag{14}$$

The signal parameters in equation (14) can be written as explicit functions of the input signal parameters and the bone-transfer function parameters. One can invert these relationships to obtain:

$$A_2 = \frac{\Delta_0^2}{4(\Omega_0^4 + \Delta_0^4)} - \frac{\sigma^2}{4(\sigma^4 + \Omega_c^4)} \quad (15)$$

$$\Phi_2 = \frac{\Omega_0^2}{4(\Omega_0^4 + \Delta_0^4)} - \frac{\Omega_c^2}{4(\sigma^4 + \Omega_c^4)} \quad (16)$$

$$A_1 = \frac{\sigma^2}{2(\sigma^4 + \Omega_c^4)} 2\pi(f_c - f_0) - 4\pi f_0 A_2 \quad (17)$$

$$\Phi_1 = \tau_0 + \frac{\Omega_c^2}{2(\sigma^4 + \Omega_c^4)} 2\pi(f_c - f_0) - 4\pi f_0 \Phi_2 \quad (18)$$

$$A_0 = a_0 - \frac{\sigma^2}{4(\sigma^4 + \Omega_c^4)} 4\pi^2(f_c - f_0)^2 - \quad (19)$$

$$\frac{1}{4} \ln\left(\frac{\sigma^4 + \Omega_c^4}{\Omega_0^4 + \Delta_0^4}\right) - A_1 2\pi f_c - A_2 4\pi^2 f_c^2$$

Each of these equations may be used sequentially to finally obtain the parameters set $\{A_2, A_1, A_0, \Phi_2, \Phi_1\}$. The expression for the phase $\Phi_0$ is not explicitly shown since it is not used in the calculation of the group-velocity.

Direct evaluation of the specific-attenuation and group-velocity functions is obtained through demodulation of the output signal s(t). To accomplish this, the signal s(t) can be passed through a rectifier and a low-pass filter to obtain the evaluation, $s_{env}(t)$:

$$S_{env}(t) = e^{-a_0}e^{-\Delta_0^2(t-\tau_0)^2} \quad (20)$$

A peak detector would provide $e^{-a_0}$ (at $t = \tau_o$) and the identification of the time at which the maximum occurs gives $\tau$ o. The time interval between the two half-peak amplitude points gives $\Delta_o^2$.

The zeros of s(t) correspond to $$\Omega_0^2(t_n - \tau_0) + \omega_0 t_n + \phi_0 = \frac{\pi}{2} + n\pi \quad (21)$$

where $t_n$ is the time at which the nth zero occurs. Then by identifying three times $t_1 < t_2 < t_3$, corresponding to three zeros of s(t), respectively, we can identify $\omega_0$ and $\Omega_0^2$:

$$\omega_0 = \pi \frac{(t_3 - t_2)(t_3 + t_2 - 2\tau_0) - (t_2 - t_1)(t_2 + t_1 - 2\tau_0)}{(t_2 - t_1)(t_3 - t_2)(t_3 - t_1)} \quad (22)$$

$$\Omega_0^2 = \pi \frac{(t_2 - t_1) - (t_3 - t_2)}{(t_2 - t_1)(t_3 - t_2)(t_3 - t_1)} \quad (23)$$

The foregoing discussion for the variations and embodiments of FIG. 2 has proceeded largely on the basis that digital processing is preferred. In contrast, the discussion for the embodiment of FIG. 3 has proceeded on the basis that analog processing is preferred. It will be understood, however that both respective embodiments and their variations can be implemented through either digital or analog techniques.

It will be seen that the described invention meets all stated objectives, with specific advantages that include but are not limited to the following:

(1) Improved signal-to-noise ratio over the prior art, which uses pulse-type input signals. In contrast, a finite-duration composite-sine wave signal is used which takes into account the spectral properties of the bony member and of the ultrasound transducers/measurement system. This allows more accurate estimates of the frequency-dependent specific attenuation function, $\mu(f)$, and frequency-dependent group-velocity function, $v_g(f)$, to be made;

(2) Incorporation of additional information not used by the prior art, which includes: (a) using both the frequency-dependent specific-attenuation, $\mu(f)$, and frequency-dependent group-velocity, $v_g(f)$, functions; (b) taking into account the frequency dependence of the group-velocity $v_g(f)$ as well as the frequency-dependence of the specific-attenuation $\mu(f)$; and (c) taking into account the nonlinear frequency-dependence of the specific-attenuation function $\mu(f)$ and/or the group-velocity function, $v_g(f)$;

(3) Use of an analytic derivation for describing the group-velocity function, $v_g(f)$. This is in contrast to the prior art which uses simple time-of-flight measurements to evaluate ultrasound velocity. Such measurements are not able to characterize the frequency-dependence of the group-velocity, nor are they able to determine at what frequency their pseudo-velocity estimates apply. In contrast, the methods described here are specifically designed to determine the frequency-dependent group-velocity function according to well-characterized mathematical relationships;

(4) Sophisticated analysis of the data, in contrast to the prior art which relies largely on simplistic univariate linear regression. In contrast, the processing described relies on neural network technology, which provides multivariate nonlinear analysis to determine the density, strength, and/or fracture risk of bone. This approach also may be regularly updated and improved, as more data becomes available;

(5) Capability to obtain in real time and with relatively simple and inexpensive analog-based technology the polynomial coefficients of the frequency-dependent specific attenuation, $\mu(f)$, and the frequency-dependent group-velocity, $v_g(f)$;

(6) Capability to correct both the frequency-dependent specific-attenuation function, $\mu(f)$, and frequency-dependent group-velocity function, $v_g(f)$, for the effects of soft tissue;

(7) Capability to assess the degree of variance of the frequency-dependent group-velocity, $v_g(f)$, and the frequency-dependent specific-attenuation, $\mu(f)$. In contrast to the prior art, which makes no attempt to adapt to the measurement conditions, this embodiment of the invention adapts to the data ensuring that high quality estimates are obtained;

(8) The nature of the apparatus as described here serves best the purposes of further experimentation and exploration for better ultrasound bone data that can be correlated for the indicated objectives. The embodiments of the invention as described above can explore a wide range of experimental configurations. Their use is expected to lead to the development of compact and efficient apparatus for obtaining the indicated objectives. For example, an analog implementation can easily be constructed if economy and simplicity are the primary objectives. Other systems which rely on analog-to-digital converters are more expensive, yet can be more flexible in terms of the type of processing which can be performed. Either type of system can either be built as a stand-alone unit or as part of a PC-based system.

What is claimed is:

1. Apparatus for non-invasively and quantitatively evaluating the status of bone tissue in vivo, as manifested through one or more of the quantities: bone-mineral density, strength and fracture risk at a given time, said apparatus comprising:

transducer means including a pair of ultrasonic transducers adapted for acoustic coupling to nearby skin and for transmission through an ascertained path which includes a bony part of a living body, signal-generator means for connection to one of said transducers to apply an excitation signal to said bony part, said excitation signal being a finite-duration signal consisting of plural frequencies that are spaced in the ultrasonic spectral region to approximately 2 MHz, said excitation signal repeating substantially in the range 1 to 1000 Hz, signal-processing means connected for response to the signal received by the other of said transducers and including means operative sequentially for averaging a succession of signals to obtain an averaged per-pulse signal, said averaging being over a predetermined period of time exceeding substantially one millisecond, means for selectively using said transducers and said excitation signal via a medium of known acoustic properties and path length to thereby establish a reference signal, said selective use being independent of coupling to the living body, means for producing the Fourier transform of said reference signal, means for producing the Fourier transform of said averaged per-pulse signal, means for comparatively evaluating said Fourier transforms to produce a bone-transfer function, means for processing said bone-transfer function to derive the frequency-dependent specific-attenuation function $\mu(f)$ and the frequency-dependent group-velocity function $v_g(f)$ associated with said bone-transfer function, and means including a neural network connected for response to said specific-attenuation function $\mu(f)$ and to said group-velocity function $v_g(f)$, said neural network being configured to generate an estimate of one or more of the said quantities.

2. Apparatus for non-invasively and quantitatively evaluating the status of bone tissue in vivo, as manifested through one or more of the quantities: bone-mineral density, strength and fracture risk at a given time, said apparatus comprising:

transducer means including a pair of ultrasonic transducers adapted for acoustic coupling to nearby skin and for transmission through an ascertained path which includes a bony part of a living body, signal-generator means for connection to one of said transducers to apply an excitation signal to said bony part, said excitation signal being a finite-duration signal consisting of plural frequencies that are spaced in the ultrasonic spectral region to approximately 2 MHz, said excitation signal repeating substantially in the range 1 to 1000 Hz, signal-processing means connected for response to the signal received by the other of said transducers and producing the Fourier transform of said received signal, means for selectively using said transducers and said excitation signal via a medium of known acoustic properties and path length to thereby establish a reference signal, said selective use being independent of coupling to the living body, means for producing the Fourier transform of said reference signal, means for comparatively evaluating said Fourier transforms to produce a bone-transfer function, further means for processing said bone-transfer function to derive the frequency-dependent specific-attenuation function $\mu(f)$ and the frequency-dependent group-velocity function $v_g(f)$ associated with said bone-transfer function, said further means including means operative sequentially for each received signal for averaging a succession of specific-attenuation functions $\mu(f)$ to obtain an averaged per-pulse specific-attenuation function $\mu(f)$, said further means also including means operative sequentially for each received pulse for averaging a succession of frequency-dependent group-velocity functions $v_g(f)$ to obtain an averaged per-pulse group-velocity function $v_g(f)$, said averaging being over a period of time exceeding substantially one millisecond, and means including a neural network connected for response to said averaged per-pulse specific-attenuation function $\mu(f)$ and to said averaged per-pulse group-velocity function $v_g(f)$, said neural network being configured to generate an estimate of one or more of the said quantities.

3. Apparatus for non-invasively and quantitatively evaluating the status of bone tissue in vivo, as manifested through one or more of the quantities: bone-mineral density, strength, and fracture risk at a given time, said apparatus comprising:

transducer means including a pair of ultrasonic transducers adapted for acoustic coupling to nearby skin and for transmission through an ascertained path which includes a bony part of a living body, signal-generator means for connection to one of said transducers to apply an excitation signal to said bony part, said excitation signal being a finite-duration signal consisting of plural frequencies that are spaced in the ultrasonic spectral region to approximately 2 MHz, said excitation signal repeating substantially in the range 1 to 1000 Hz, signal-processing means connected for response to the signal received by the other of said transducers and producing the Fourier transform of each said received signal, means for selectively using said transducers and said excitation signal via a medium of known acoustic properties and path length to thereby establish a reference signal, said selective use being independent of coupling to the living body, means for producing the Fourier transform of said reference signal, further means for comparatively evaluating said Fourier transforms to produce a bone-transfer function calculation for each said received signal, said further means including means operative sequentially for each received signal for averaging a succession of bone-transfer function calculations to obtain an averaged per-pulse bone-transfer function, said averaging being for a period of time exceeding substantially one millisecond, said further means including means for processing said averaged per-pulse bone-transfer function to derive the frequency-dependent specific-attenuation function $\mu(f)$ and the frequency-dependent group-velocity function $v_g(f)$ associated with said averaged per-pulse bone-transfer function, and means including a neural network connected for response to said specific-attenuation function $\mu(f)$ and to said group-velocity function $v_g(f)$, said neural network being configured to generate an estimate of one or more of the said quantities.

4. Apparatus for non-invasively and quantitatively evaluating the status of bone tissue in vivo, as manifested through one or more of the quantities: bone-mineral density, strength and fracture risk at a given time, said apparatus comprising:

transducer means including a pair of ultrasonic transducers adapted for acoustic coupling to nearby skin and for transmission through an associated path which includes a bony part of a living body;

signal-generator means for connection to one of said transducers to apply an excitation signal to said bony part, said excitation signal being a finite-duration composite sine-wave signal meeting the requirements of the following relationship:

$$v(t) = \sum_{i=0}^{N} a_i \sin(2\pi f_i t + \phi_i), \quad 0 \leq t \leq T \quad (1)$$

where $a_i$ and $\phi_i$ are the amplitude and phase, respectively, associated with frequency $f_i$, $i = 1, \ldots, N$, and T is chosen to be at least two times longer than the period of the lowest frequency $f_i$, where said composite sine-wave signal consists of plural discrete frequencies that are spaced in the ultrasonic spectral region to approximately 2 MHz; and where the amplitudes $a_i$ are chosen according to the relationship:

$$a_i \propto \frac{\exp(Bf_i)}{|H_r(f_i)|} \quad (2)$$

wherein B is the attenuation of an average bony member and $|H_r(f_i)|$ is the magnitude transfer function of the overall ultrasound measurement system when a medium of negligible attenuation is placed between the two transducers;

signal-processing means connected for response to the signal received by the other of said transducers and including means operative sequentially for each received signal for averaging a succession of signals to obtain an averaged per-pulse signal, each averaging being over a predetermined minimum period of time exceeding substantially one millisecond, means for selectively using said transducers and said excitation signal via a medium of known acoustic properties and path length to thereby establish a reference signal, said selective use being independent of coupling to the living body, means for separately storing said reference signal, and means for comparatively evaluating said averaged per-pulse signal against said stored reference signal.

5. Apparatus according to any one of claims 1, 2 or 3, in which said finite-duration signal is a composite sine-wave signal consisting of a plurality of discrete frequencies.

6. Apparatus according to claim 4 or claim 1, wherein said signal-processing means includes on-line operative means for appraising the degree of variance of the currently averaged received signal, said appraisal being for the shorter one of two time values namely, (a) the time required to achieve a predetermined minimum variance, and (b) a predetermined maximum period of time.

7. Apparatus according to claim 2, wherein said further means includes on-line operative means for appraising the degree of variance of the currently averaged per-pulse specific-attenuation function $\mu(f)$ associated with said bone-transfer function, said appraisal being for the shorter one of two time values, namely, (a) the time required to achieve a predetermined minimum variance, and (b) a predetermined maximum period of time.

8. Apparatus according to claim 2, wherein said further means includes on-line operative means for appraising the degree of variance of the currently averaged per-pulse group-velocity function $v_g(f)$ associated with said bone transfer function, said appraisal being for the shorter one of two time values, namely, (a) the time required to achieve a predetermined minimum variance, and (b) a predetermined maximum period of time.

9. Apparatus according to claim 2, wherein said further means includes first on-line operative means for appraising the degree of variance of the currently averaged per-pulse specific-attenuation function $\mu(f)$ associated with said bone-transfer function, and wherein said further means also includes second on-line operative means for appraising the degree of variance of the currently averaged per-pulse group-velocity function $v_g(f)$ associated with said bone-transfer function; said appraisals being for the shorter one of two time values, namely, (a) the time required to achieve a predetermined minimum variance for both of said appraisals, and (b) a predetermined maximum period of time.

10. Apparatus according to claim 3, wherein said further means includes on-line operative means for appraising the degree of variance of the currently averaged bone-transfer function, said appraisal being for the shorter one of two time values, namely, (a) the time required to achieve a predetermined minimum variance, and (b) a predetermined maximum period of time.

11. Apparatus according to any one of claims 1–4, wherein one of said transducers is adapted for transmit/receive functioning, and wherein said signal-processing means is adapted to evaluate the round-trip travel time for a near-surface echo from the bone, whereby to generate a measurement of traversed soft-tissue thickness, wherein said traversed soft-tissue thickness is used to correct said specific-attenuation and said group-velocity functions for the effects of the soft-tissue.

12. Apparatus according to any one of claims 1–4, wherein said transducer means includes a separate further transducer adapted for transmit/receive functioning, and wherein said signal-processing means is adapted to evaluate the round-trip travel time for a near-surface echo from the bone, whereby to generate a measurement of traversed soft-tissue thickness, wherein said traversed soft-tissue thickness is used to correct said specific-attenuation and said group-velocity functions for the effects of the soft-tissue.

13. Apparatus according to any one of claims 1–4, wherein said transducer means includes two separate transducers adapted for transmit/receive functioning and spaced from each other for differently directed response aspects on the bony part, and wherein said signal-processing means is adapted to evaluate the round-trip travel time for the respective near-surface echoes from the bone for each of said response aspects, whereby to generate measurement of traversed soft-tissue thickness for each of the respective response aspects, wherein said traversed soft-tissue thickness is used to correct said specific-attenuation and said group-velocity functions for the effects of the soft-tissue.

14. Apparatus according to any one of claims 1-4, wherein each of said transducers is adapted for transmit/receive functioning, and wherein said signal-processing means is adapted to evaluate the round-trip travel time for a near-surface echo from the bone to one of said transducers, said signal-processing means being also adapted to evaluate the round-trip travel time for a near-surface echo from the bone to the other of said transducers, whereby to generate measurement of traversed soft-tissue thickness on opposite sides of the bone, wherein said traversed soft-tissue thickness is used to correct said specific-attenuation and said group-velocity functions for the effects of the soft-tissue.

15. Apparatus according to any one of claims 1, 2 and 3, wherein each of said frequency-dependent functions, namely $\mu(f)$ and $v_g(f)$, is processed in polynomial form involving a finite set of coefficients for each polynomial, and means for supplying polynomial coefficients as inputs to said neural network.

16. Apparatus according to any one of claims 1, 2 and 3, wherein each of said frequency-dependent quantities, namely $\mu(f)$ and $v_g(f)$, is processed in polynomial form involving a finite set of coefficients for each polynomial, and means for supplying polynomial coefficients as inputs to said neural network, said polynomial coefficients being for polynomial orders in the range 0 to 4.

17. Apparatus according to any one of claim 4, 1, 2 and 3, wherein said neural network is adapted to receive further inputs selected from the group comprising: age, sex, weight, height, bone-tissue thickness, overall tissue thickness, mental status, and bone-densitometric measurements.

18. The method of non-invasively and quantitatively evaluating the status of bone tissue in vivo, as manifested through one or more of the quantities: bone-mineral density, strength and fracture risk, using a neural network and two ultrasonic transducers that are non-invasively adapted for acoustic coupling to nearby skin and for transmission through a bony part of a living body, which method comprises the steps of:

(a) acoustically coupling said transducers to nearby skin on opposite sides of said bony part;
(b) driving one of said transducers with a finite-duration excitation signal consisting of plural frequencies that are spaced in the ultrasonic spectral region to approximately 2 MHz, and repeating said excitation signal at a rate in the range 1 to 1000 Hz, whereby the other transducer is acoustically subjected to said signal after transmission through said bony part, thereby producing a bone-transmitted electrical-output signal for each excitation signal;
(c) sequentially processing each electrical-output signal by averaging a succession of signals to obtain an averaged per-pulse signal, each averaging being over a predetermined period of time exceeding substantially one millisecond;
(d) selectively using said transducers and said excitation signal via a medium of known acoustic properties and path length, said selective use being independent of coupling to the living body, whereby to establish a reference signal, and separately storing the reference signal;
(e) producing separate Fourier transforms of said reference signal and of said bone-transmitted signal, and comparatively evaluating said Fourier transforms to produce a bone-transfer function;
(f) processing the bone-transfer function to derive the frequency-dependent specific-attenuation function $\mu(f)$ and the frequency-dependent group-velocity function $v_g(f)$ associated with the bone-transfer function; and
(g) configuring the neural network to generate from said frequency-dependent specific-attenuation function $\mu(f)$ and from said frequency-dependent group-velocity function $v_g(f)$ an estimate of one or more of said quantities.

19. The method of non-invasively and quantitatively evaluating the status of bone tissue in vivo, as manifested through one or more of the quantities: bone-mineral density, strength and fracture risk, using a neural network and two ultrasonic transducers that are non-invasively adapted for acoustic coupling to nearby skin and for transmission through a bony part of a living body, which method comprises the steps of:

(a) acoustically coupling said transducers to nearby skin on opposite sides of said bony part;
(b) driving one of said transducers with a finite-duration excitation signal consisting of plural frequencies that are spaced in the ultrasonic spectral region to approximately 2 MHz, and repeating said excitation signal at a rate in the range 1 to 1000 Hz, whereby the other transducer is acoustically subjected to said signal after transmission through the bony member, thereby producing a bone-transmitted electrical-output signal for each excitation signal;
(c) sequentially processing each electrical output signal to produce the Fourier transform thereof;
(d) selectively using said transducers and said excitation signal via a medium of known acoustic properties and path length, said selective use being independent of coupling to the living body, whereby to establish a reference signal, and separately producing and storing the Fourier transform of said reference signal;
(e) comparatively evaluating said Fourier transforms to produce a bone-transfer function;
(f) processing the frequency-dependent specific-attenuation $\mu(f)$ and the frequency-dependent group-velocity function $v_g(f)$ associated with the bone-transfer function;
(g) processing a succession of specific-attenuation functions $\mu(f)$ to obtain an averaged per-pulse specific-attenuation function $\mu(f)$, and processing a corresponding succession of frequency-dependent group-velocity functions $v_g(f)$ to obtain an averaged per-pulse group-velocity function $v_g(f)$, said averaging being over a period of time exceeding substantially one millisecond; and
(h) configuring the neural network to generate from said averaged per-pulse specific-attenuation function $\mu(f)$ and from said averaged per-pulse group-velocity function $v_g(f)$ an estimate of one or more of said quantities.

20. The method of claim 18 or claim 19, in which said excitation signal is a composite sine-wave signal consisting of a plurality of discrete frequencies.

21. Apparatus for non-invasively and quantitatively evaluating the status of bone tissue in vivo, as manifested through one or more of the quantities: bone mineral density, strength and fracture risk at a given time, said apparatus comprising:

transducer means including a pair of ultrasonic transducers adapted for acoustic coupling to nearby skin and for transmission through an ascertained path which includes a bony part of a living body,     signal-generator means for connection to one of said transducers to apply an excitation signal to said bony part, said excitation signal being configured to produce a Gaussian amplitude modulated sinusoidal waveform in the ultrasonic spectral region to approximately 2 MHz, said excitation signal repeating substantially in the range 1 to 1000 Hz,     signal processing means connected for response to the signal received by the other of said transducers, and including means for demodulating said signal,     means for extracting the set of demodulated signal parameters, including means for averaging a succession of said signal parameters to obtain an averaged per-pulse signal parameter set,     means for selectively using said transducers and said excitation signal via a medium of known acoustic properties and path length to thereby establish a reference signal, said selective use being independent of coupling to the living body,     means for demodulating said reference signal, including means for extracting the set of demodulated reference signal parameters,     means for deriving from the demodulated signal parameter set and the demodulated reference signal parameter set the polynomial coefficients of the frequency-dependent specific-attenuation function, $\mu(f)$, and the polynomial coefficients of the bone-transfer function phase, $\Phi(f)$,     means for deriving from the bone transfer function phase, $\Phi(f)$, the frequency-dependent group-velocity, $v_g(f)$,     means including a neural network connected for response to said finite set of polynomial coefficients for $\mu(f)$ and group velocity function, said neural network being configured to generate an estimate of one or more of the said quantities.

22. Apparatus according to claim 21, wherein said excitation being configured to produce a sinusoidally amplitude modulated sinusoidal waveform in the ultrasonic spectral region up to 2 MHz, said excitation signal repeating substantially in the range 1 to 1000 Hz.

23. Apparatus according to claim 21, wherein said excitation being configured to produce a sinusoidally frequency modulated sinusoidal waveform in the ultrasonic spectral region up to 2 MHz, said excitation signal repeating substantially in the range 1 to 1000 Hz.

24. Apparatus according to claim 21, wherein said excitation being configured to produce a sinusoidally amplitude modulated and sinusoidally frequency modulated sinusoidal waveform in the ultrasonic spectral region up to 2 MHz, said excitation signal repeating substantially in the range 1 to 1000 Hz.

25. Apparatus according to claim 21, wherein said excitation signal being configured to produce a superposition of Gaussian amplitude modulated sinusoidal waveforms containing multiple frequencies in the ultrasonic frequency range up to 2 MHz, said excitation signal repeating substantially in the range 1 to 1000 Hz.

26. Apparatus according to claim 21, wherein said excitation signal being configured to produce a Gaussian amplitude modulated sinusoidal waveform consisting of a sequentially applied set of multiple frequencies in the ultrasonic frequency range up to 2 MHz, said excitation signal repeating substantially in the range 1 to 1000 Hz.

27. Apparatus according to claim 21, wherein said coefficients of the frequency-dependent specific-attenuation function are constrained by $\mu_2=0$.

28. Apparatus according to claim 21, wherein said coefficients of the bone-transfer function phase are constrained as $\Phi_2=0$.

29. Apparatus according to claim 21, wherein both the said coefficients of the specific-attenuation function polynomial, and the said coefficients of the bone-transfer function phase are constrained as $\mu_2=0$ and $\Phi_2=0$.

30. Apparatus according to claim 21, wherein said demodulation and derivation of the polynomial coefficients of $\mu(f)$ and group velocity function, $v_g(f)$, are carried out in real time.

31. The method of non-invasively and quantitatively evaluating the status of bone tissue in vivo, as manifested through one or more of the quantities: bone-mineral density, strength and fracture risk, using a neural network and two ultrasonic transducers that are non-invasively adapted for acoustic coupling to nearby skin and for transmission through a bony part of a living body, which method comprises the steps of:

(a) acoustically coupling said transducers to nearby skin on opposite sides of said bony part;

(b) driving one of said transducers with an excitation signal consisting of frequencies that are spaced in the ultrasonic spectral region to approximately 2 MHz, and repeating said excitation signal at a rate in the range 1 to 1000 Hz, whereby the other transducer is acoustically subjected to said signal after transmission through a bony member, thereby producing a bone-transmitted electrical-output signal for each excitation signal, said excitation signal being configured such that said bone-transmitted signal possesses a Gaussian envelope;

(c) sequentially demodulating each electrical-output signal to produce a set of demodulated bone-transmitted signal parameters;

(d) selectively using said transducers and said excitation signal via a medium of known acoustic properties and path length, said selective use being independent of coupling to the living body whereby to establish a reference signal, and separately demodulating and storing the demodulated reference signal parameter set;

(e) processing the demodulated bone-transmitted signal parameters and demodulated reference-signal parameters to produce the frequency-dependent specific-attenuation function, $\mu(f)$, and frequency-dependent group-velocity function, $v_g(f)$;

(f) processing a succession of specific-attenuation functions $\mu(f)$ to obtain an averaged per-pulse specific-attenuation function $\mu(f)$, and processing a corresponding succession of frequency-dependent group-velocity functions $v_g(f)$ to obtain an averaged per-pulse group-velocity function $v_g(f)$, said averaging being over a period of time exceeding substantially one millisecond; and     (g) configuring the neural network to generate from said averaged per-pulse specific-attenuation function $\mu(f)$ and from said averaged per-pulse group-velocity function $v_g(f)$ an estimate of one or more of the said quantities.

32. The method of non-invasively and quantitatively evaluating the status of bone tissue in vivo, as manifested through one or more of the quantities: bone-mineral density, strength and fracture risk, using two ultrasonic transducers that are non-invasively adapted for acoustic coupling to nearby skin and for transmission through a bony part of a living body, which method comprises the steps of:

(a) acoustically coupling said transducers to nearby skin on opposite sides of said bony part;

(b) driving one of said transducers with a finite-duration composite sine-wave excitation signal meeting the requirements of the following relationship:

$$v(t) = \sum_{i=0}^{N} a_i \sin(2\pi f_i t + \phi_i), \quad 0 \leq t \leq T \quad (1)$$

where $a_i$ and $\phi_i$ are the amplitude and phase, respectively, associated with frequency $f_i$, $i=1,\ldots,N$, and T is chosen to be at least two times longer than the period of the lowest frequency $f_i$; where said composite sine-wave signal consists of plural discrete frequencies that are spaced in the ultrasonic spectral region to approximately 2 MHz and repeating said excitation signal at a rate in the range 1 to 1000 Hz; and where the amplitudes $a_i$ are chosen according to the relationship:

$$a_i \propto \frac{\exp(Bf_i)}{|H_r(f_i)|} \quad (2)$$

wherein B is the attenuation of an average bony member and $|H_r(f_i)|$ is the magnitude transfer function of the overall ultrasound measurement system when a medium of negligible attenuation is placed between the two transducers; whereby the other transducer is acoustically subjected to said signal after transmission through said bony part, thereby producing a bone-transmitted electrical-output signal for each excitation signal;

(c) sequentially processing each electrical-output signal by averaging a succession of signals to obtain an averaged per-pulse signal, each averaging being over a predetermined minimum period of time exceeding substantially one millisecond;

(d) selectively using said transducers and said excitation signal via a medium of known acoustic properties and path length, said selective use being independent of coupling to the living body, whereby to establish a reference signal;

(e) separately storing the reference signal; and (f) comparatively evaluating the averaged per-pulse signal against the stored reference signal.

* * * * *